(12) United States Patent
Johnson et al.

(10) Patent No.: US 12,023,165 B2
(45) Date of Patent: Jul. 2, 2024

(54) SCREENING CARDIAC CONDITIONS USING CARDIAC VIBRATIONAL ENERGY SPECTRAL HEAT MAPS

(71) Applicant: Northwestern University, Evanston, IL (US)

(72) Inventors: Ethan M. I. Johnson, Evanston, IL (US); Michael Markl, Chicago, IL (US)

(73) Assignee: Northwestern University, Evanston, IL (US)

(*) Notice: Subject to any disclaimer, the term of this patent is extended or adjusted under 35 U.S.C. 154(b) by 197 days.

(21) Appl. No.: 17/452,139

(22) Filed: Oct. 25, 2021

(65) Prior Publication Data

US 2022/0125367 A1 Apr. 28, 2022

Related U.S. Application Data

(60) Provisional application No. 63/104,745, filed on Oct. 23, 2020.

(51) Int. Cl.
*A61B 5/347* (2021.01)
*A61B 5/0205* (2006.01)
*A61B 5/11* (2006.01)
*A61B 5/308* (2021.01)
*A61B 5/349* (2021.01)

(52) U.S. Cl.
CPC ............ *A61B 5/347* (2021.01); *A61B 5/0205* (2013.01); *A61B 5/11* (2013.01); *A61B 5/308* (2021.01); *A61B 5/349* (2021.01)

(58) Field of Classification Search
None
See application file for complete search history.

(56) References Cited

U.S. PATENT DOCUMENTS

| 6,978,184 | B1 | 12/2005 | Marcus | |
|---|---|---|---|---|
| 8,700,137 | B2 | 4/2014 | Albert | |
| 2004/0111025 | A1* | 6/2004 | Avniash | A61B 8/543 600/428 |
| 2006/0122525 | A1* | 6/2006 | Shusterman | A61B 5/6822 600/513 |
| 2011/0295127 | A1* | 12/2011 | Sandler | A61B 5/318 600/528 |

(Continued)

FOREIGN PATENT DOCUMENTS

EP 3463066 A1 4/2019

OTHER PUBLICATIONS

Ashouri H, Orlandic L, Inan O. Unobtrusive estimation of cardiac contractility and stroke volume changes using ballistocardiogram measurements on a high bandwidth force plate. Sensors (Basel). 16:787, 2016.

(Continued)

*Primary Examiner* — Ankit D Tejani
(74) *Attorney, Agent, or Firm* — Quarles & Brady LLP

(57) ABSTRACT

Described here are systems and methods for generating cardiac vibrational energy spectral ("VIBES") heat maps from physical vibration data and cardiac cycle timing data measured from a subject. Quick screening for heart valve, cardiovascular, and/or cardiothoracic abnormalities can be provided based on an analysis and/or classification of the generated VIBES heat maps.

17 Claims, 8 Drawing Sheets
(5 of 8 Drawing Sheet(s) Filed in Color)

(56) References Cited

U.S. PATENT DOCUMENTS

2015/0038856 A1     2/2015   Houlton et al.

OTHER PUBLICATIONS

Becker M, Roehl A, Siekmann U, Koch A, de la Fuente M, Roissant R, Radermacher K, Marx N, Hein M. Simplified detection of myocardial ischemia by seismocardiography. Herz. 39:586-592, 2014.

Bogaert J, Dymarkowski S, Taylor AM, Muthurangu V, Clinical cardiac MRI. Springer Science & Business Media, 2012.

Castiglioni P, Faini A, Parati G, DiRienzo M. Wearable seismocardiography. Conf Proc IEEE Eng Med Biol Soc. pp. 3954-3957, 2007.

DiRienzo M, Vaini E, Castiglioni P, Merati G, Meriggi P, Parati G, Faini A, Rizzo F. Wearable seismocardiography: Towards a beat-by-beat assessment of cardiac mechanics in ambulant subjects. Auton Neurosci. 178:50-59, 2013.

Earls JP, Ho VB, Foo TK, Castillo E, Flamm SD. Cardiac mri: recent progress and continued challenges. J Magn Reson Imaging. 16:111-127, 2002.

Etemadi M, Inan OT. Wearable ballistocardiogram and seismocardiogram systems for health and performance. J Appl Physiol. 124:452-461, 2017.

Frahm J, Merboldt K, Bruhn H, Gyngell M, Hanicke W, Chien D. 0.3-second flash mri of the human heart. Magn Reson Med. 13:150-157, 1990.

Glover G, Pelc N. A rapid-gated cine mri technique. Magn Reson Annu 1988.

Goda MA, Hajas P. Morphological determination of pathological pcg signals by time and frequency domain analysis. Comput Cardiol. pp. 1133-1136, 2016.

Hope MD, Meadows AK, Hope TA, Ordovas KG, Saloner D, Reddy GP, Alley MT, Higgins CB. Clinical evaluation of aortic coarctation with 4d flow mr imaging. J Magn Reson Imaging. 31:711-718, 2010.

Hundley WG, et al, 2010. "ACCF/ACR/AHA/NASCI/SCMR 2010 expert consensus document on cardiovascular magnetic resonance: a report of the American College of Cardiology Foundation Task Force on Expert Consensus Documents". Journal of the American College of Cardiology, 55(23), pp. 2614-2662.

Inan O, Etemadi M, Paloma A, Giovangrandi L, Kovacs G. Non-invasive cardiac output trending during exercise recovery on a bathroom-scale-based ballistocardiograph. Physiol Meas. 30:261, 2009.

Inan OT, Baran Pouyan M, Javaid AQ, Dowling S, Etemadi M, Dorier A, Heller JA, Bicen AO, Roy S, DeMarco T et al. Novel wearable seismocardiography and machine learning algorithms can assess clinical status of heart failure patients. Circ Heart Fail. 11:e004313, 2018.

Inan OT, Migeotte PF, Park KS, Etemadi M, Tavakolian K, Casanella R, Zanetti J, Tank J, Funtova I, Prisk GK et al. Ballistocardiography and seismocardiography: A review of recent advances. IEEE J Biomed Health Inform. 19:1414-1427, 2014.

Jerosch-Herold M, Zanetti J, Merkle H, Poliac L, Huang H, Mansoor A, Zhao F, Wilke N. The seismocardiogram as magnetic-field-compatible alternative to the electrocardiogram for cardiac stress monitoring. Int J Cardiovasc Imaging. 15:523-531, 1999.

Johnson EMI, et al, 2019. "Seismocardiography and 4D flow MRI reveal impact of aortic valve replacement on chest acceleration and aortic hemodynamics." Journal of Cardiac Surgery.

Jung BA, Hennig J, Scheffler K. Single-breathhold 3d-truefisp cine cardiac imaging. Magn Reson Med. 48:921-925, 2002.

Larson AC, White RD, Laub G, McVeigh ER, Li D, Simonetti OP. Self-gated cardiac cine mri. Magn Reson Med. 51:93-102, 2004.

Marcus FI, Sorrell V, Zanetti J, Bosnos M, Baweja G, Perlick D, Ott P, Indik J, He DS, Gear K. Accelerometer-derived time intervals during various pacing modes in patients with biventricular pacemakers: Comparison with normals. Pacing Clin Electrophysiol. 30:1476-1481, 2007.

Markl M, Frydrychowicz A, Kozerke S, Hope M, Wieben O. 4d flow mri. J Magn Reson Imaging. 36:1015-1036, 2012.

Markl M, Schnell S, Barker AJ. 4d flow imaging: current status to future clinical applications. Curr Cardiol Rep. 16:481, 2014.

Markl M, Wallis W, Harloff A, 2011. "Reproducibility of flow and wall shear stress analysis using flow-sensitive four-dimensional MRI." Journal of Magnetic Resonance Imaging, 33(4), pp. 988-994.

Mohiaddin RH, Firmin DN, Longmore DB. Age-related changes of human aortic flow wave velocity measured noninvasively by magnetic resonance imaging. J Appl Physiol. 74:492-497, 1993.

Nishimura RA, et al, 2014. "2014 AHA/ACC guideline for the management of patients with valvular heart disease: a report of the American College of Cardiology/American Heart Association Task Force on Practice Guidelines". Journal of the American College of Cardiology, 63(22), pp. e57-e185.

Roldán-Alzate A, Frydrychowicz A, Niespodzany E, Landgraf BR, Johnson KM, Wieben O, Reeder SB. In vivo validation of 4d flow mri for assessing the hemodynamics of portal hypertension. J Magn Reson Imaging. 37:1100-1108, 2013.

Stankovic Z, Allen BD, Garcia J, Jarvis KB, Markl M. 4d flow imaging with mri. Cardiovasc Diagn Ther. 4:173, 2014.

Starr I, Rawson A, Schroeder H, Joseph N. Studies on the estimation of cardiac ouptut in man, and of abnormalities in cardiac function, from the heart's recoil and the blood's impacts; the ballistocardiogram. Am J Physiol. 127:1-28, 1939.

Tariq U, Hsiao A, Alley M, Zhang T, Lustig M, Vasanawala SS. Venous and arterial flow quantification are equally accurate and precise with parallel imaging compressed sensing 4d phase contrast mri. J Magn Reson Imaging. 37:1419-1426, 2013.

Tavakolian K, Blaber AP, Ngai B, Kaminska B. Estimation of hemodynamic parameters from seismocardiogram. Comput Cardiol. pp. 1055-1058, 2010.

Tavakolian K, Ngai B, Akhbardeh A, Kaminska B, Blaber A. Comparative analysis of infrasonic cardiac signals. Comput Cardiol. pp. 757-760, 2009.

Van der Geest RJ, Reiber JH. Quantification in cardiac mri. JMRI. 10:602-608, 1999.

Zhang X, Durand L, Senhadji L, Lee HC, Coatrieux JL. Time-frequency scaling transformation of the phonocardiogram based of the matching pursuit method. IEEE Trans Biomed Eng. 45:972-979, 1998.

Zoghbi WA, et al, 2017. "Recommendations for noninvasive evaluation of native valvular regurgitation: a report from the American Society of Echocardiography developed in collaboration with the Society for Cardiovascular Magnetic Resonance". Journal of the American Society of Echocardiography, 30(4), pp. 303-371.

* cited by examiner

SCREENING CARDIAC CONDITIONS USING CARDIAC VIBRATIONAL ENERGY SPECTRAL HEAT MAPS

CROSS-REFERENCE TO RELATED APPLICATIONS

This application claims the benefit of U.S. Provisional Patent Application Ser. No. 63/104,745, filed on Oct. 23, 2020, and entitled "SCREENING CARDIAC CONDITIONS USING CARDIAC VIBRATIONAL ENERGY SPECTRAL HEAT MAPS," which is herein incorporated by reference in its entirety.

BACKGROUND

Abnormal cardiac and flow function can go undetected until serious adverse health complications arise. For example, congenital heart defects may in many cases not be diagnosed until adulthood. These defects may manifest firstly in abnormal flow, and they may not register in easily-acquired physiologic measurements such as pulse oximetry. Accurate assessment requires sophisticated medical imaging and trained interpretation, which incurs high health care utilization and associated costs.

During a normal cardiac cycle, mechanical forces from the beating heart and highly pulsatile aortic blood flow are transmitted through the chest wall. Components of these forces are detectable outside the body with simple methods; for example, stethoscopes have long been used to listen to heart sounds. A full spectrum of mechanical forces can be reliably detected by external chest-acceleration measurements to form a signal known as a seismocardiogram ("SCG") that characterizes the cardiac reverberations.

Seismocardiography—and related concepts such as ballistocardiography and phonocardiography that also interpret physiological meaning from extracorporeally measured physical vibrations—are subjects of study with extended histories of exploration for potential clinical utility. Interpretations of many aspects of seismocardiography have been validated, in some cases through comparison to a "gold standard" reference measurement, and in some through phenomenological characterization from induced physiologic change to observed measurement change.

These interpretations include many important quantitative indicators of cardiac function, such as changing pre-ejection period or cardiac output. There remain parameters of physiology with clinical relevance, such as aortic blood velocities, for which quantitative relationships have not been firmly established. This stems partially from variegated body structures in a general population, which complicate the transfer function from cardiac activity to detectable vibration, but also partially from the difficulty of obtaining comprehensive reference measurements for use in quantitation.

Magnetic resonance imaging ("MRI"), as a non-invasive method for interrogating physiology, offers the ability to visualize morphology and function of soft tissues, including the heart, with granular detail. Cine MRI, in particular, can be used to obtain relatively high temporal-resolution characterization of cardiac motion. Flexibility in orientation of views allows for capturing many aspects of motion, including ventricular contraction and valve motion. By delineating tissue boundaries in images, dynamic quantification of volumes can be performed, and advances in automated image segmentation techniques contribute to reliability of quantitation. Time-resolved three-dimensional phase-contrast (4D flow) MRI, as another MR technique, can directly measure and depict blood movement throughout the body, such as in the thoracic aorta. Flow through an area of interest can be directly calculated from measured blood velocities. Although 4D flow scans can be time consuming to perform, protocols have been developed with adequate robustness to permit clinical use of 4D flow MRI.

Overall, imaging by cardiac MRI gives extensive characterization of cardiac function and flow, and it is a valuable tool in assessing heart disease. However, performing MR scans and 4D flow analysis incur a variety of significant costs, stemming in part from MR machine usage and computationally-demanding 4D flow analysis, and their use is best deployed strategically.

There is a lack of low-cost easy-to-use technology for reliably detecting cardiac function and flow abnormalities, such as congenital heart deformations or altered aortic flow function. Medical imaging tests such as ultrasound and MRI are highly informative for these diseases, but their use is not completely routine due to the need for trained operators and interpretation of acquired images to yield results, and the high costs associated as a result. For these reasons, a technique for inexpensively and quickly determining presence or absence of potential flow abnormalities, necessitating comprehensive cardiac MRI, would be valuable.

SUMMARY OF THE DISCLOSURE

The present disclosure addresses the aforementioned drawbacks by providing a method for generating a cardiac vibrational energy spectral heat map. The method includes accessing physical vibration signal data with a computer system, where the physical vibration signal data indicate physical vibrations measured from a subject, which indicate cardiac motion of the subject. Cardiac cycle timing data are also accessed with the computer system, where the cardiac cycle timing data indicate at least one of a timing or a duration of an event within a cardiac cycle of the subject. A spectral energy map is then computed with the computer system, where the spectral energy map is computed from the physical vibration signal data acquired over a period of time determined from the cardiac cycle timing data. The spectral energy map is compared to normative data, generating output as a cardiac vibrational energy spectral ("VIBES") heat map that indicates deviations in vibration energy levels relative to the normative data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
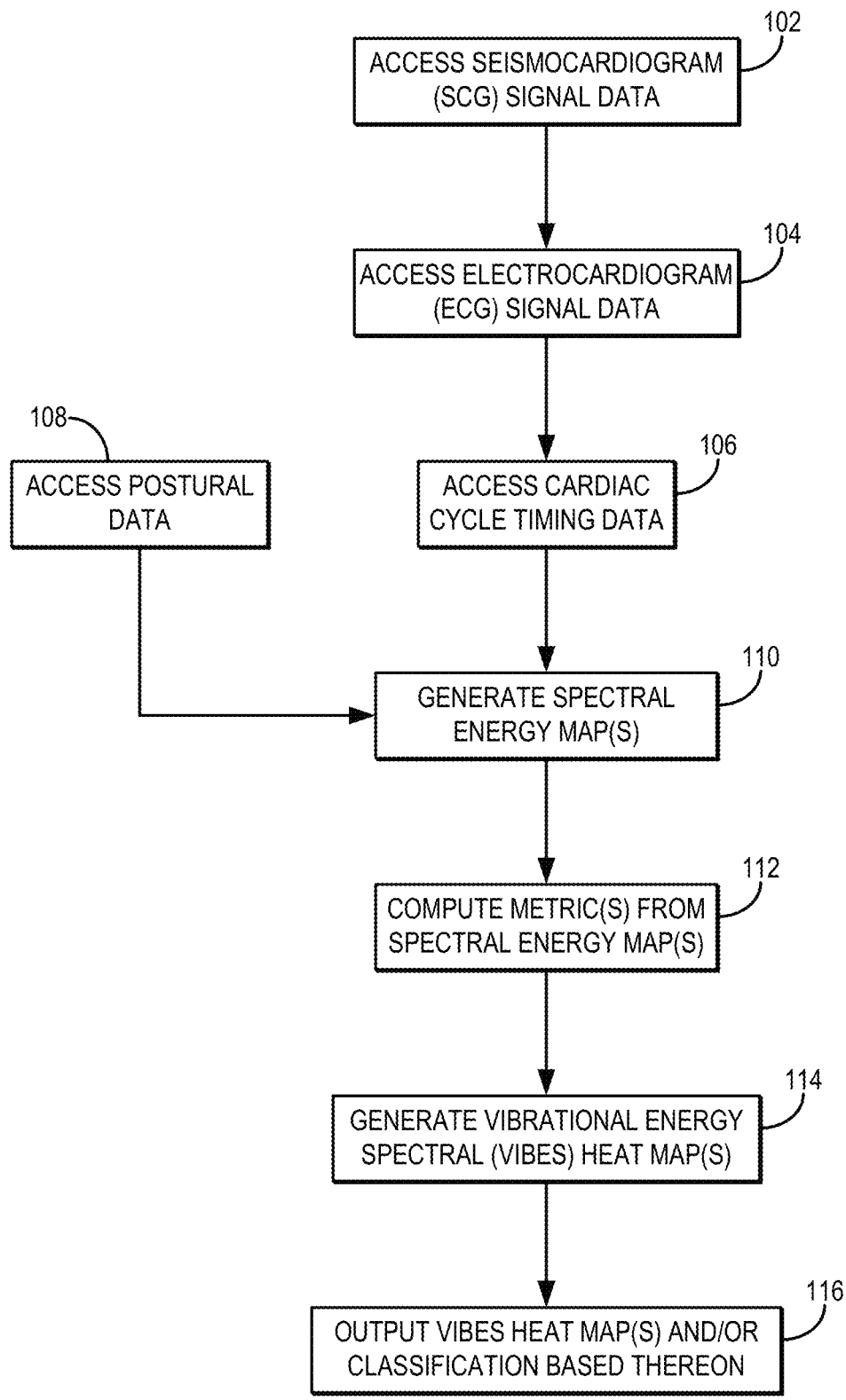
FIG. 1 is a flowchart setting forth the steps of an example method for generating a cardiac vibrational energy spectral ("VIBES") heat map, which can be used to classify a cardiac condition of the subject.

Described here are systems and methods for generating vibrational energy spectral ("VIBES") heat maps from physical vibration data and electrocardiography ("ECG") data measured from a patient. These systems and methods enable quick screening for heart valve, cardiovascular, and/or cardiothoracic abnormalities based on an analysis and/or classification of the generated VIBES heat maps. In this way, the systems and methods described in the present disclosure can be used to support a clinical screening protocol for congenital heart abnormalities; to detect aortic flow or cardiac function abnormalities in patients with suspected heart or valvular disease; or to otherwise screen a patient based on a measured heart condition. This technology can be integrated with a medical imaging service to improve patient throughput by preselecting subjects most likely to benefit from comprehensive examination.

As a general example, the systems and methods described in the present disclosure allow for the identification of potential cardiac abnormalities by using advanced processing of vibrations, creating a cardio VIBES heat map, from a quick measurement on the surface of the chest, which can potentially be used to avoid expensive imaging tests when unnecessary. The measured vibrational signals are highly sensitive to abnormal flow and cardiac function without the need for subject baseline calibration or long-term monitoring. As a result, the systems and methods described in the present disclosure can be used to reliably preselect patients that truly need more comprehensive examination. Advantageously, the described cardio VIBES technology can enable more universal screening for cardiac abnormalities at low cost, and can streamline the clinical care for patients with known abnormalities that require long-term monitoring.

As noted, the systems and methods described in the present disclosure can be implemented for prescreening of a variety of heart valve, cardiovascular, and/or cardiothoracic conditions. The non-invasive nature of the techniques make them well-suited to patient populations that may otherwise be difficult to screen, monitor, and/or diagnose, including pediatric patients. Advantageously, the systems and methods described in the present disclosure can be implemented in an outpatient/office setting and/or in a patient's home.

As opposed to traditional ECG, the systems and methods described in the present disclosure can be implemented without a trained physician, thereby enabling a patient to monitor their heart condition in an at-home setting. The described cardio VIBES technology can implement a simple measurement technique, with no operator training required, to give clinically valuable insights about cardiac and flow function. The analysis component, for instance, can be fully automated, and the results can be presented in an intuitive manner that allows for quick clinical decision-making. Furthermore, the measurement and analysis of data can be implemented using inexpensive electronics and can also be transmitted over communication networks with minimal bandwidth requirements (e.g., the data sizes can be less than 1% of a typical 5-10 megapixel photo, such as on the order of a few hundred kilobytes or less). Use of the described cardio VIBES technology can, therefore, streamline clinical care for patients with cardiovascular disease by simplifying the long-term management and allowing expensive imaging tests to be tailored to the patients' clinical needs. As one example use case, a patient can be monitored on a monthly basis, with magnetic resonance imaging ("MRI") follow up as needed based on the output generated using the systems and methods described in the present disclosure.

In general, the systems and methods described in the present disclosure enable quick, non-invasive testing or screening for heart valve, cardiovascular, and/or cardiothoracic abnormalities from easy-to-acquire simultaneous physical vibration and ECG signals on the surface of the chest combined with information about cardiac cycle timing events. The screening can be performed by placing a device on the chest to record the physical vibration and ECG signals, then processing those signals to generate subject-specific VIBES heat maps.

The movement of the beating heart and pulsatile blood flow through the thoracic arteries create characteristic vibration signatures, and measurement of these (via the VIBES heat maps) can detect abnormalities in heart valve, cardiovascular, and/or cardiothoracic function and flow that would otherwise require sophisticated medical imaging to identify. The cardio VIBES techniques described in the present disclosure provide an inexpensive and easy-to-use technology that provides quick, high-sensitivity testing for heart valve, cardiovascular, and/or cardiothoracic abnormalities, and can be used as a valuable tool for improving and/or streamlining clinical care for patients with several types of cardiovascular disease.

Referring now to FIG. 1, a flowchart is illustrated as setting forth the steps of an example method for generating and classifying or otherwise analyzing vibrational energy spectral ("VIBES") heat maps, where the VIBES heat maps are generated from physical vibration and ECG data measured from a subject.

In general, indicators of abnormalities of the heart and vessels can be derived from spectral analysis of infrasonic or low-frequency chest vibrations together with cardiac timing references, such as the duration of systole, the timing of ECG waveform components, and/or the timing of heart valve movements. The resulting VIBES heat maps, which are indicative of non-normative vibrational energy spectra, can be created to highlight potential cardiothoracic abnormalities. For instance, the VIBES heat maps are sensitive to altered cardiac and/or aortic function, and can therefore be analyzed to detect abnormalities such as aortic stenosis from aortic valve calcification or helical flow caused by congenital valve malformations.

Incorporating multiple timing references allows higher specificity of interpretation. For example, vibrational energy levels can be measured at mid-systole in a limited frequency band to identify aortic flow abnormalities.

The method includes accessing physical vibration signal data as seismocardiogram ("SCG") signal data with a computer system, as indicated at step 102. More generally, SCG signal data or other suitable cardiac vibration signal data that are indicative of physical vibrations occurring in a subject as a result of cardiac motion, can be accessed with the computer system. Accessing these data may include retrieving previously acquired data from a memory or other data storage device or medium. Additionally or alternatively, accessing these data may include acquiring the data with one or more vibration sensors and communicating or otherwise transferring the data to the computer system. In general, the SCG signal data are representative of physical vibrations or movements at the surface of the chest near the heart. The vibration sensors may include accelerometers, gyroscopes, or combinations thereof. In some instances, the vibration sensor(s) may include accelerometers and/or gyroscopes in a cellular smart-phone.

The method also includes accessing electrocardiogram ("ECG") signal data with the computer system, as indicated at step 104. Accessing these data may include retrieving previously acquired data from a memory or other data storage device or medium. Additionally or alternatively, accessing these data may include acquiring the data with one or more ECG leads and communicating or otherwise transferring the data to the computer system.

Preferably, the SCG signal data and the ECG signal data are contemporaneous with each other, such that the data are, or were, acquired from the subject during the same time period. As one non-limiting example, SCG signal data and ECG signal data can be recorded using a wearable cardiac sensor that incorporates a MEMS accelerometer (ADXL355, Analog Devices, USA) for acquiring SCG signal data as chest acceleration measurements and an integrated circuit analog-to-digital converter (ADS1292, Texas Instruments, USA) for acquiring ECG signal data, and the sensor samples can be recorded by a microcontroller (Amtel SAM4L8) and stored in non-volatile memory. The device can be operated with a 1 kHz sampling rate and 2 μm s$^{-2}$ sensitivity. When recording SCG signal data, the device can be placed at the sternum with the subject in a supine position.

In addition to the SCG signal data and ECG signal data, cardiac cycle timing data are also be accessed with the computer system, as indicated at step 106. Accessing these data may include retrieving previously acquired data from a memory or other data storage device or medium. Additionally or alternatively, accessing these data may include computing, extracting, or otherwise determining cardiac cycle timing information from one or more data sources. In general, the cardiac cycle timing information can include timing and duration of systole; timing and duration of diastole; peak-systole time; cardiac valve movements, such as valve opening times and valve closing times; and timing and duration of the ECG complexes, including ECG intervals and ECG wave durations (e.g., P, Q R, S, and/or T waves; QRS complex; PR segment; ST segment; PR interval; QT interval).

In some instances, the cardiac cycle timing data can be computed, extracted, or otherwise determined from the SCG signal data, the ECG signal data, or both. For instance, the cardiac cycle timing information can include timing features that have been extracted from SCG signal data and/or ECG signal data, which may include the SCG signal data accessed in step 102 and/or the ECG signal data accessed in step 104.

As another example, the cardiac cycle timing data can include cardiac cycle timing information determined from cardiac ultrasound data. For example, cardiac cycle timing information can be determined from M-mode ultrasound of the cardiac valves, which can then be annotated by a user or via an automated process. Cardiac ultrasound can also be used to estimate other quantities and timing parameters, such as dynamic ventricular volumes, systole duration, and stroke volumes.

As still another example, the cardiac cycle timing data can include cardiac cycle timing information determined from cine cardiac magnetic resonance images. For instance, short-axis cine images can be analyzed to contour the left ventricle and myocardium in each frame and slice. Contours can be generated by an automated function, and manual adjustments can be made to remove contours from slices shown as being above the mitral valve or below the apex in the four-chamber view. From these contours, the left-ventricular volume ("LVV") can be determined as the net volume contained, exclusive of the myocardium. The duration of systole ($T_{sys}$) can be defined as the time elapsed between the first ECG-gated frame and the one in which minimal LVV was observed. From visual inspection of two-chamber, three-chamber, four-chamber, and left-ventricular outflow tract cine images, the times of opening and closing of the aortic and mitral valves can also be determined. The valve opening/closing events can also be determined using automated image processing methods. As one non-limiting example, the cine images can be input to a suitably trained machine learning algorithm, generating output as labeled images and/or feature data indicating the timing and/or presence of valve opening/closing events. Examples of such techniques are described by V. P. Kamphuis, et al., in "Automated Cardiac Valve Tracking for Flow Quantification with Four-dimensional Flow MRI," *Radiology*, 2019; 290 (1):70-78, and by O. Bernard, et al., in "Deep Learning Techniques for Automatic MRI Cardiac Multi-Structures Segmentation and Diagnosis: Is the Problem Solved?," *IEEE Trans Med Imaging*, 2018; 37(11):2514-2525.

Additionally, several features, such as maximal flow rate and stroke volume, can be calculated from derived aortic flow and ventricular volume dynamics. Examples of cardiac MRI features that can be determined include ejection fraction; maximal ejection and filling rates; stroke volume; and extrema of cut-plane-averaged or cut-plane-aggregated blood velocities, accelerations, and flow rates.

In some instances, postural data of the subject can also be accessed with the computer system, as indicated at step 108. The postural data can include information about the subject's posture (e.g., prone, standing) and the direction of gravity during acquisition of the SCG and/or ECG signal data. These postural data can be used to rotate and/or rescale directional components of the vibration signals contained in the SCG signal data. Using posture information can advantageously permit standardization of energy levels from measurements taken in different settings. As a non-limiting example, the postural data can be obtained from accelerometry data with a gravity offset, or can be externally specified (e.g., by the operator taking the measurement).

Using the SCG signal data, the ECG signal data, and the cardiac cycle timing data, one or more spectral energy maps are then generated, as indicated at process block 110. Spectral decomposition of the chest vibrations in the SCG signal data is performed to analyze vibrational energy levels at different cardiac times and in different frequency ranges. In general, a spectral energy map can be generated by calculating time-limited and band-limited energy represented in the vibration signal (e.g., a short-time Fourier transform or wavelet transform) for the duration of signals recorded. Optionally, postural data can be used to perform a decomposition of the physical vibrations in the SCG signal data to adjust multi-axis measurements for the subject posture (e.g., rotating to align gravity with a fixed axis). Information about the cardiac cycle can then be integrated to form a cardiac time-referenced spectral energy map.

Metrics of the energy levels can be calculated for the vibrations that are referenced to cardiac time, as indicated at step 112. For example, average vibrational energy in the 60-120 Hz range during the middle-half of systole can be calculated, or peak vibrational energy in the 120-240 Hz range over the half-systole duration preceding aortic valve closure can be calculated. The average and/or peak vibrational energy can also be calculated in other frequency ranges, some of which may or may not be overlapping frequency ranges, and during other cardiac phases. For instance, vibrational energy metrics may be calculated in the 10-60 Hz range, the 40-80 Hz range, the 60-120 Hz range, the 120-240 Hz range, or different ranges within and/or overlapping these disclosed ranges. These metrics can be computed beat-by-beat or they can be computed from a beat-averaged spectral energy map. The vibrational energy metrics can include average vibrational energy, peak vibrational energy, or other suitable spectral energy metrics, including root-mean-squared ("RMS") energy.

As an example, SCG acceleration signal features can be calculated. For instance, beat-to-beat chest accelerations can be assembled from SCG recordings by time-referencing measurements to R-waves detected in simultaneously-acquired ECG signal data. R-waves can be identified by automated peak-detection of wavelet-decomposed ECG signal (e.g., order-4 Daubechies, approximate 8-20 Hz bands, minimal peak separation 0.3 s). From beat-synchronized net acceleration magnitudes, $a_i(t)$, for i=1, . . . , $n_b$ set on a time scale from to zero to 80 percent of the median R-R interval, various different analyses can be performed.

As one example, beat-mean SCG accelerations can be computed as, $$a(t) = \frac{1}{n_b} \sum_{i=1}^{n_b} a_i(t). \tag{1}$$

As another example, beat-mean acceleration spectra can also be computed. For instance, the short-time Fourier transform ("STFT") can be computed for each beat in order to generate acceleration spectra as, $$s_i(t,f) = \text{STFT}(a_i(t)) \tag{2}.$$

The average in magnitude across beats can then be computed to find a beat-mean acceleration spectrum. In one non-limiting example, a Hamming window can be used for the STFT. For example, a 0.2 s Hamming window may be used. 100441 The average energies in several time-frequency regions can be calculated. This is analogous to computing the root-mean-squared SCG acceleration over limited time and frequency ranges. The time regions used can include, for example, early and late systole and diastole, with "early" and "late" being considered half of systole duration at the beginning or end of the period (i.e., if systole commences with the R-wave at t=0 and ends at t=1, then the time regions considered were the steps of 0.5 from –0.5 to 1.5). As one non-limiting example, the frequency regions used can include [10,60] Hz ("low-f"), [60,120] Hz ("med-f"), and [120,240] Hz ("hi-f").

Figure 2:
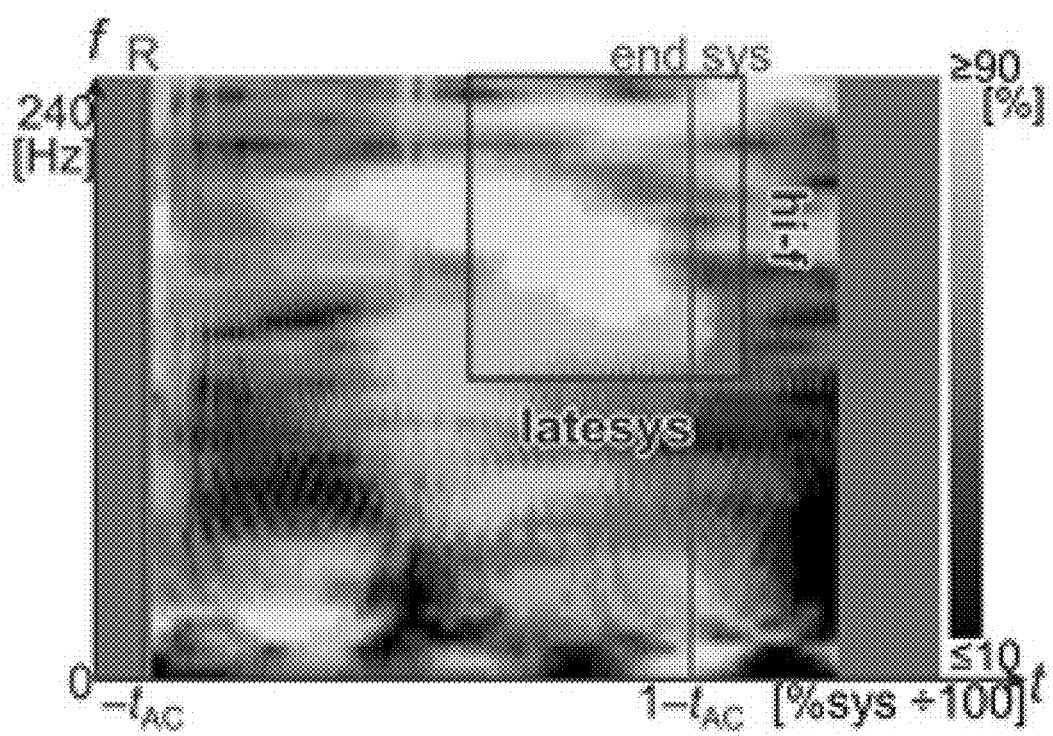
FIG. 2 is an example of a VIBES heat map.

The spectral energy map(s) and/or the energy level metrics computed therefrom can then be compared to normative data in order to generate a classification that the underlying SCG signal data, ECG signal data, or both, include an indication of a cardiac abnormality, as indicated at step 114. Additionally or alternatively, the spectral energy map(s) can also be compared to other imaging or physiological measurement data associated with the cardiovascular system, such as cardiac and 4D flow magnetic resonance images and/or parameters determined from such images. The output of this comparison can include a vibrational energy spectral ("VIBES") heat map, which indicates deviations or other comparisons relative to the normative data. For instance, the VIBES heat map may depict a distance metric computed between the subject's spectral energy map (or metric computed therefrom) and normative data. As an example, as described above, the average SCG energy levels in time and frequency bins can be calculated, and normative comparisons to calculations from a database of cardiac-time rescaled SCG signals from a reference population can be made, with scores derived based on energy level percentiles and output as the VIBES heat map. An example VIBES heat map is shown in FIG. 2.

The normative data may include data associated with expected normal cardiac function in a healthy patient. As one example, this normative data can be provided from a database of measured, normal cardiac function (e.g., via normal SCG signal data, normal ECG signal data, or both), which may have been reported in previous clinical or scientific studies. In examples where the spectral energy map(s) and/or the energy level metrics are compared to normative data, the suitable correlation or other algorithm can be used to identify significant changes in the subject's cardiac function relative to the normative data. By comparing the spectral energy map(s) and/or the energy level metrics to normative data, it is contemplated that additional information about the subject can be provided to the clinician.

For example, if comparing the spectral energy map(s) and/or the energy level metrics to normative data indicates a significant deviation from the normative data, this deviation can be quantified or qualified and presented to the clinician. Such deviations provide information to a clinician that may indicate an underlying cardiac issues, such as an undiagnosed cardiovascular and/or cardiothoracic condition, or the like.

Similarly, the normative data may be indicative of a particular cardiovascular and/or cardiothoracic condition, such that correlation of the spectral energy map(s) and/or the energy level metrics to the normative data can quantify or qualify a probability that the underlying SCG signal data and/or ECG signal data are indicative of the particular cardiovascular and/or cardiothoracic condition.

For instance, in an example study, chest vibrations, ECG, and cardiovascular MRI were obtained from several healthy subjects without cardiovascular disease. The subjects' ECG R-waves, the duration of systole shown in MRI, and the time of mitral and aortic valve opening and closings were registered and a spectral decomposition of the chest vibrations was performed, as described above, to analyze vibrational energy levels at different cardiac times and in different frequency ranges. The same measurements were collected and the same analysis was performed in patients with known valvular cardiovascular disease history. This analysis revealed high sensitivity to aortic flow abnormalities associated with the cardiovascular disease in these patients. The metrics can also be referenced to demographic information, such as age-, sex-, and/or body-size-normative values. Additionally, the metrics may be calibrated against established metrics of cardiac and flow function to estimate other functional metrics of the heart and vessels that are of clinical interest, such as cardiac output, peak aortic velocity, wall-shear stress, mean pressure gradient, and pulse wave velocity.

Baseline dynamic quantiles can also be formed various ways. As one example, dynamic quantiles can be formed by time-aligning measurements across subjects only to the ECG R-wave, which may create a broader peak. As another example, dynamic quantiles can be formed by aligning measurements to all cardiac valve events, which may result in a narrower peak.

From these normative ranges, abnormal energy heat maps for selected subjects can be generated and output to a user or stored for later use, as indicated at step 116. As an example, the abnormal energy heat maps can show at each time and frequency the highest decile with energy lower than observed in the subject recording. The results of analysis can be presented immediately as a VIBES map via a graphical user interface or other interactive system, or they can be stored for later review. Results can be presented as absolute energy levels or demographic-normalized ranges.

A classification can also be made based on the VIBES heat map and output to a user. For instance, an indication can be made based on a VIBES heat map that the subject should receive follow up testing or imaging, and this indication can be output to a user, such as via a graphical user interface.

Figure 3:
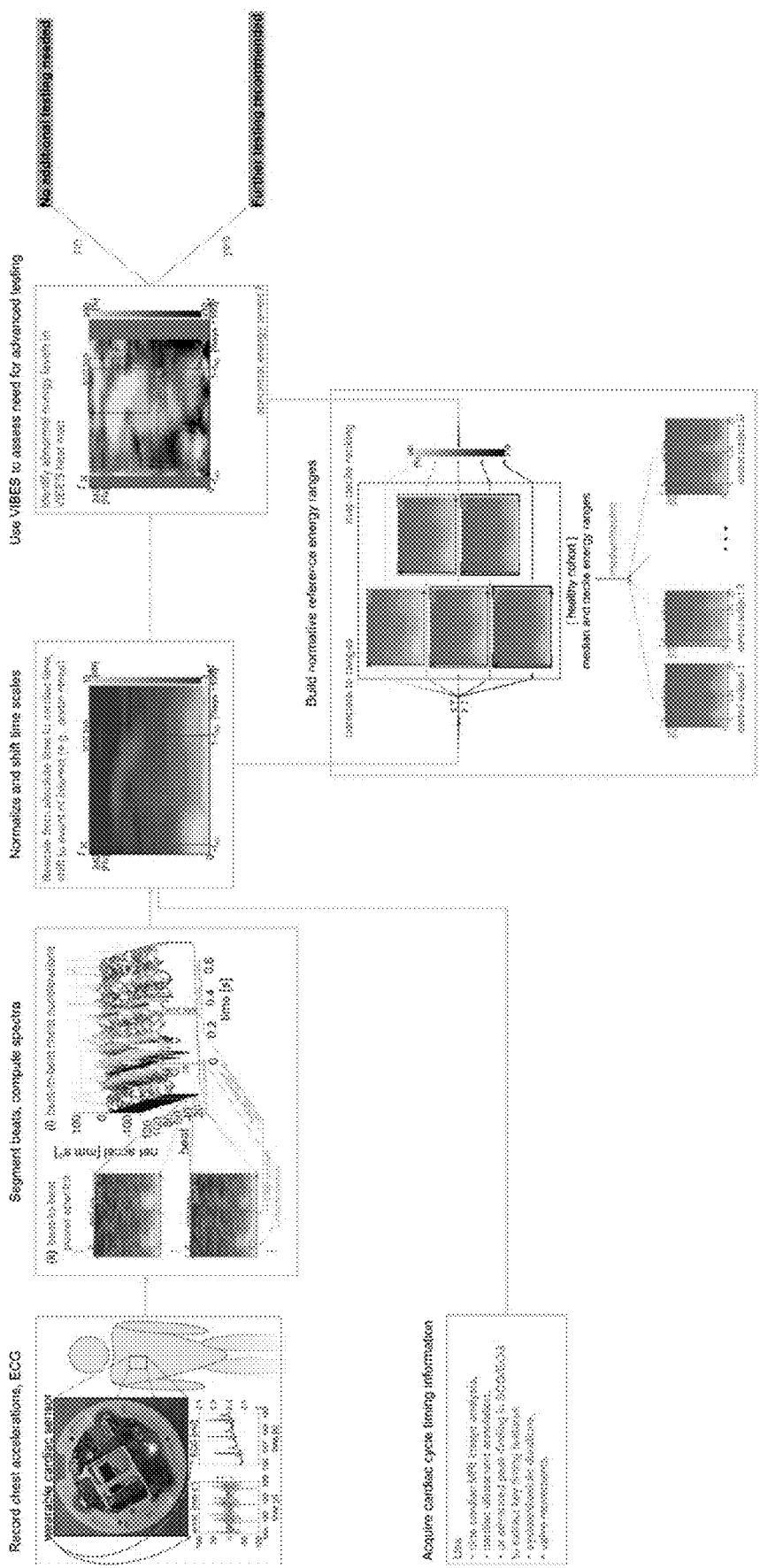
FIG. 3 shows an example workflow for generating and classifying a VIBES heat map.

An example workflow for computing and classifying VIBES heat map(s) is shown in FIG. 3.

Figure 4:
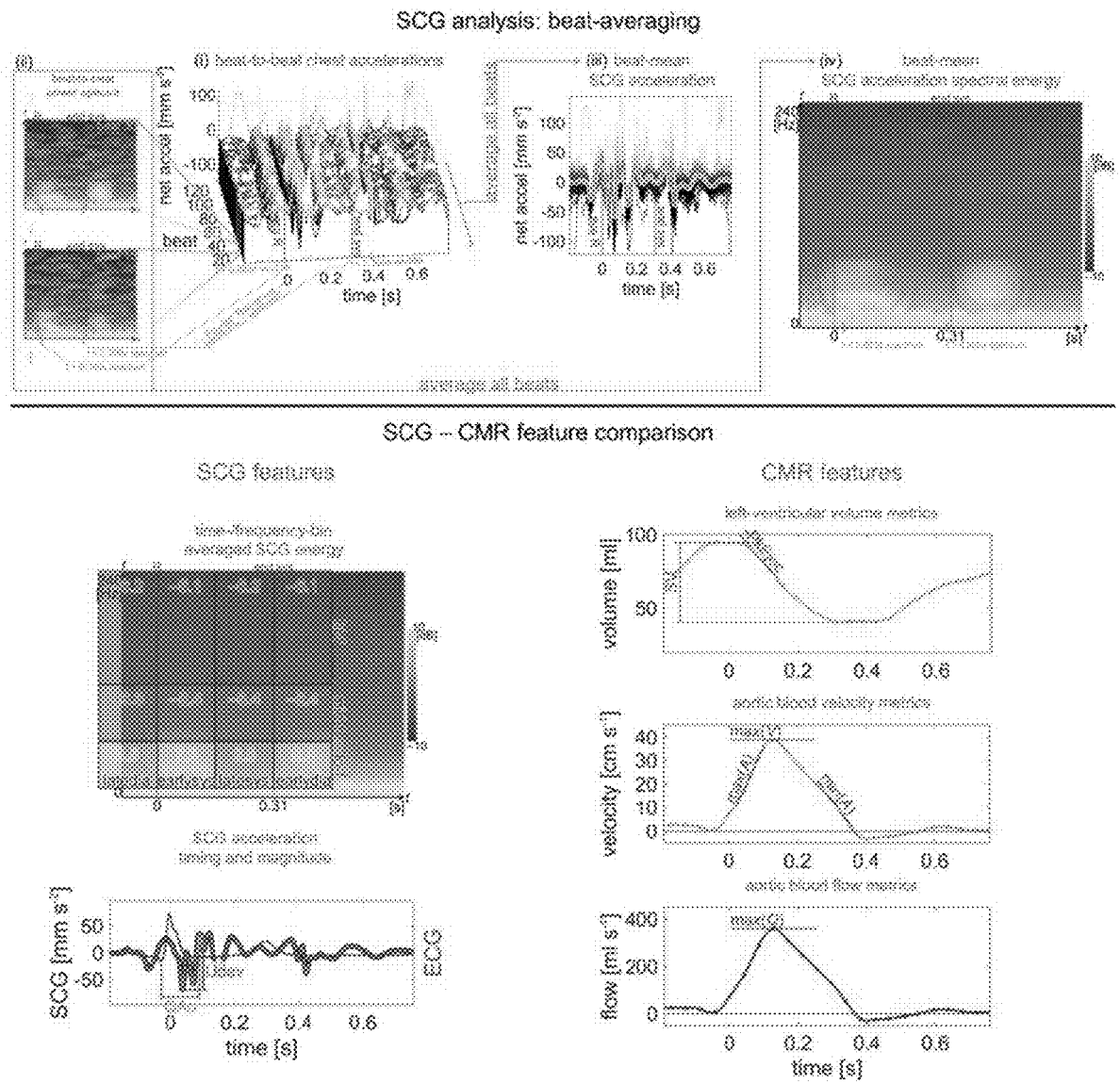
FIG. 4 shows example metrics that can be used for comparison of SCG and cardiac MRI.

FIG. 4 illustrates example metrics that can be used for comparison of SCG and CMR. The beat-synchronized acceleration measurements (left, i) were decomposed by STFT for each beat (left, ii) and averaged across beats to find each a characteristic SCG spectrum (left, iii). The average energies in several time-frequency regions were used as features for comparison. Two example reference time markings (0.025 s, 0.030 s) are shown to illustrate correspondences between recorded acceleration and decomposed short-time spectra. CMR metrics of cardiac and flow function, such as stroke volume, maximal ejection rate, maximal blood velocity, extremal blood accelerations, and maximal flow (right) are calculated from the processed CMR images.

Figure 5:
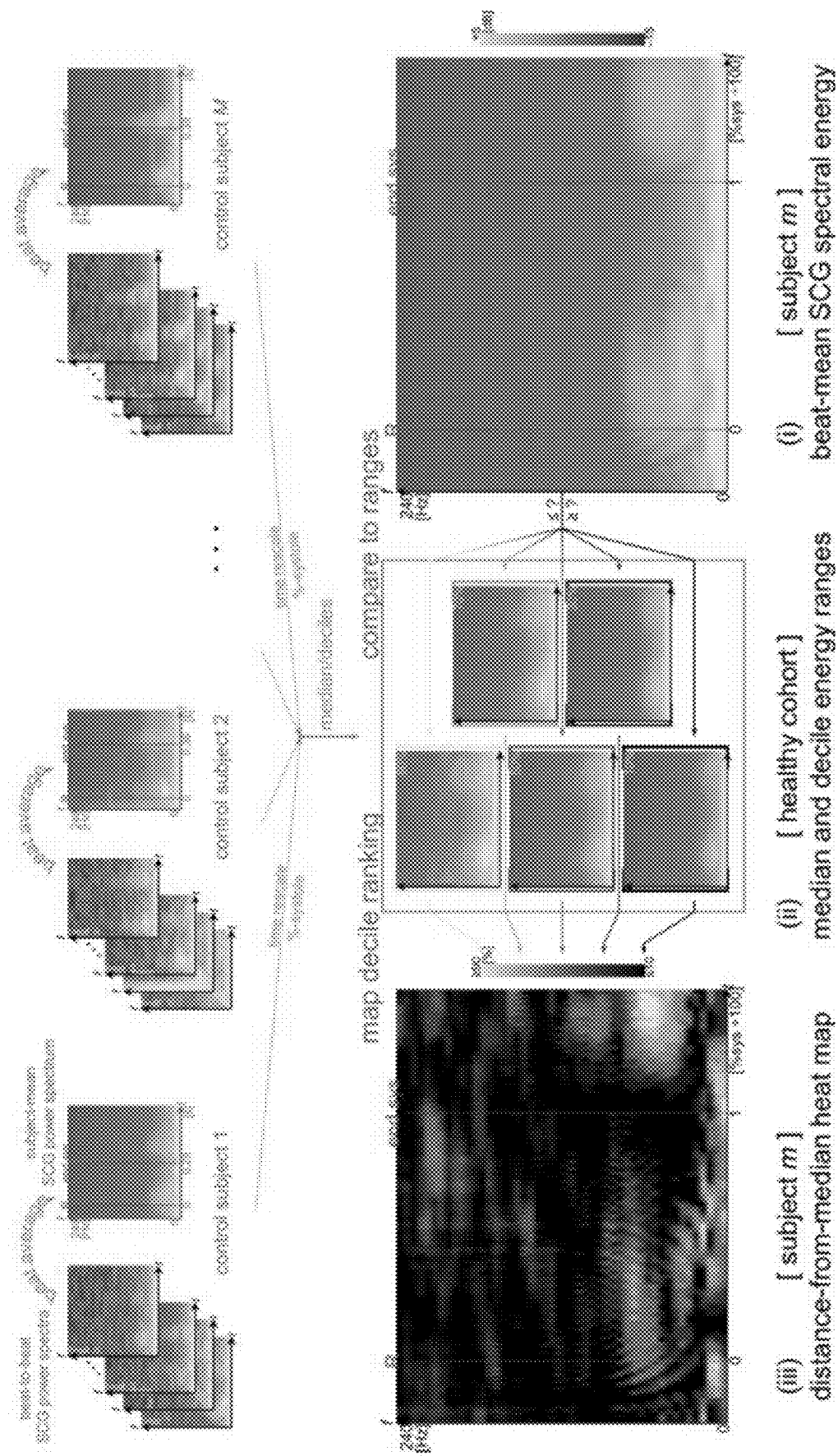
FIG. 5 shows example normative median and decile ranges for SCG energies that are aggregated from beat-averaged SCG spectra of a healthy cohort.

FIG. 5 shows example normative median and decile ranges for SCG energies (middle) that were aggregated from the beat-averaged SCG spectra of a healthy cohort (top). Individual subjects' SCG energies (right) were compared to the quantiles to classify each frequency and time point according to deciles of energy levels. Decile rankings were coded into heat maps (left) indicating distance from the median, so that for example, a frequency and time point with SCG power exceeding that of 90% of the normal cohorts' powers is shown light pink; and, conversely, a point at which the power is less than 90% of the normal cohorts' powers (10% decile) is shown black.

Figure 6:
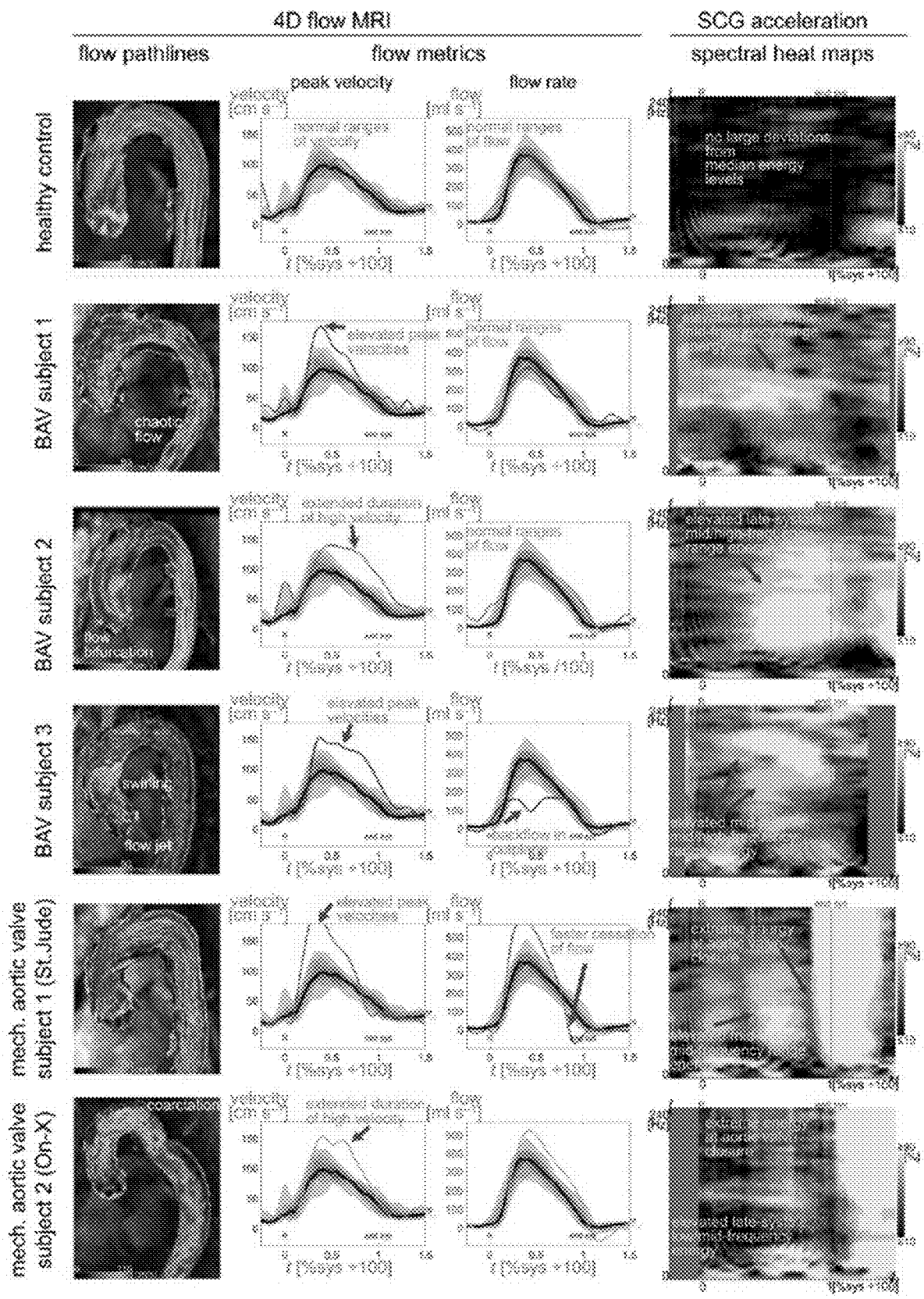
FIG. 6 shows example analyses from 4D flow MRI and SCG VIBES heat maps for various subject cohorts.

FIG. 6 shows example analyses from 4D flow MRI (left 3 columns) and SCG VIBES heat maps (right column) from one randomly-selected healthy control (top row), three BAV subjects (middle 3 rows), and two mechanical valve subjects (bottom 2 rows) with different implants (brand names listed for each). The third mechanical valve subject had the same valve brand as the first, and the subjects had similar flow and energy deviations. Velocity and flow quantifications are from a cut-plane in the ascending aorta.

Figure 7:
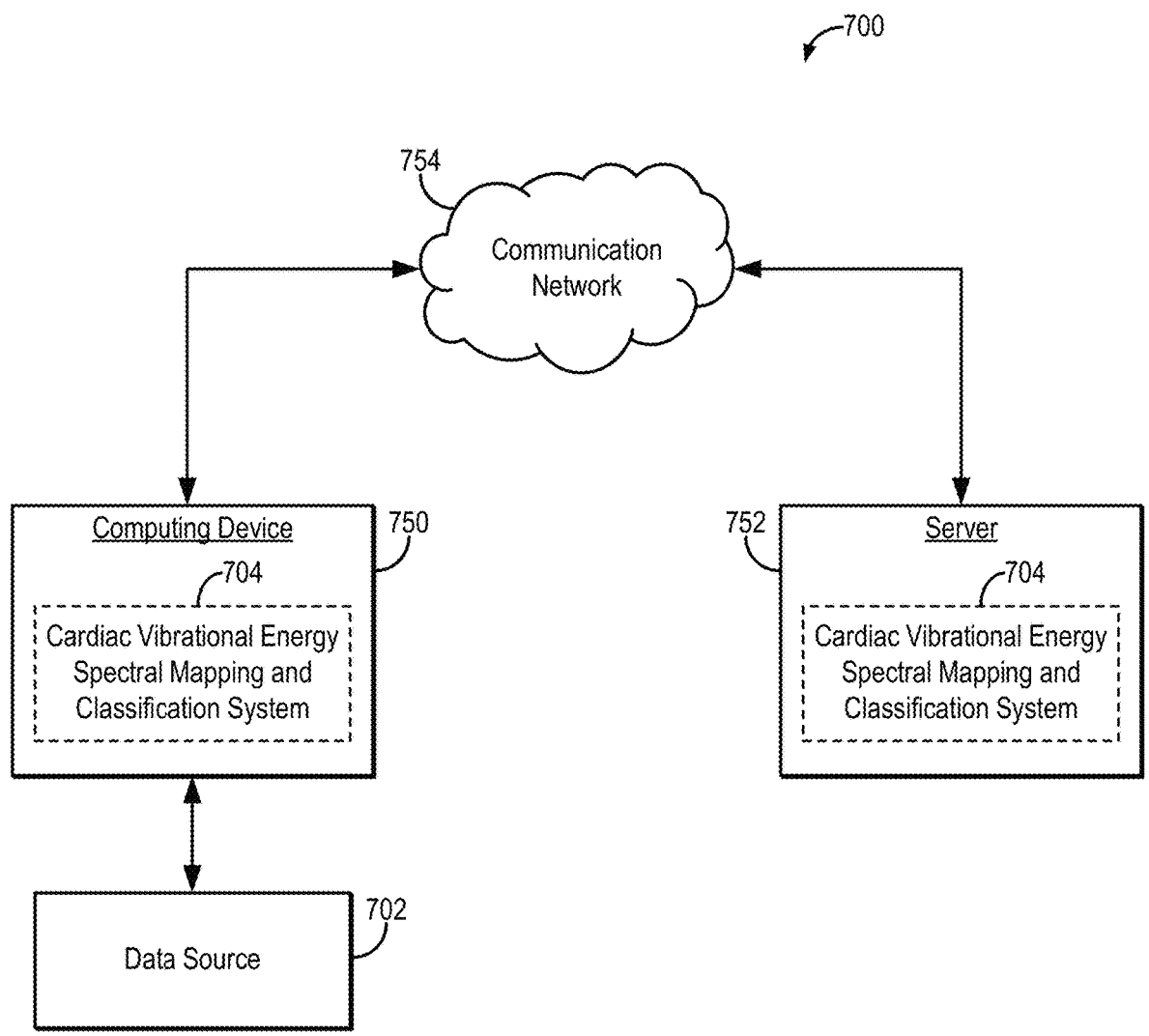
FIG. 7 is a block diagram illustrating an example cardiac VIBES heat map generating and classifying system.

Referring now to FIG. 7, an example of a system 700 for generating and classifying vibrational energy spectral ("VIBES") heat maps in accordance with some embodiments of the systems and methods described in the present disclosure is shown. As shown in FIG. 7, a computing device 750 can receive one or more types of data (e.g., SCG signal data, ECG signal data, cardiac cycle timing data) from data source 702, which may be an SCG and/or ECG data source. In some embodiments, computing device 750 can execute at least a portion of a cardiac vibrational energy spectral mapping and classification system 704 to generate and classify VIBES heat maps from data received from the data source 702.

Additionally or alternatively, in some embodiments, the computing device 750 can communicate information about data received from the data source 702 to a server 752 over a communication network 754, which can execute at least a portion of the cardiac vibrational energy spectral mapping and classification system. In such embodiments, the server 752 can return information to the computing device 750 (and/or any other suitable computing device) indicative of an output of the cardiac vibrational energy spectral mapping and classification system 704.

In some embodiments, computing device 750 and/or server 752 can be any suitable computing device or combination of devices, such as a desktop computer, a laptop computer, a smartphone, a tablet computer, a wearable computer, a server computer, a virtual machine being executed by a physical computing device, and so on. The computing device 750 and/or server 752 can also compute metrics and generate maps or other images from the data.

In some embodiments, data source 702 can be any suitable source of data (e.g., SCG signal data, ECG signal data, cardiac cycle timing data), such as a wearable cardiac sensor that is capable of measuring both physical vibrations and electrocardiograms, another computing device (e.g., a server storing data), and so on. In some embodiments, data source 702 can be local to computing device 750. For example, data source 702 can be incorporated with computing device 750 (e.g., computing device 750 can be configured as part of a device for capturing, scanning, and/or storing measurement data and/or images). As another example, data source 702 can be connected to computing device 750 by a cable, a direct wireless link, and so on. Additionally or alternatively, in some embodiments, data source 702 can be located locally and/or remotely from computing device 750, and can communicate data to computing device 750 (and/or server 752) via a communication network (e.g., communication network 754).

In some embodiments, communication network 754 can be any suitable communication network or combination of communication networks. For example, communication network 754 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 754 can be a local area network, a wide area network, a public network (e.g., the Internet), a private or semi-private network (e.g., a corporate or university intranet), any other suitable type of network, or any suitable combination of networks. Communications links shown in FIG. 7 can each be any suitable communications link or combination of communications links, such as wired links, fiber optic links, Wi-Fi links, Bluetooth links, cellular links, and so on.

Figure 8:
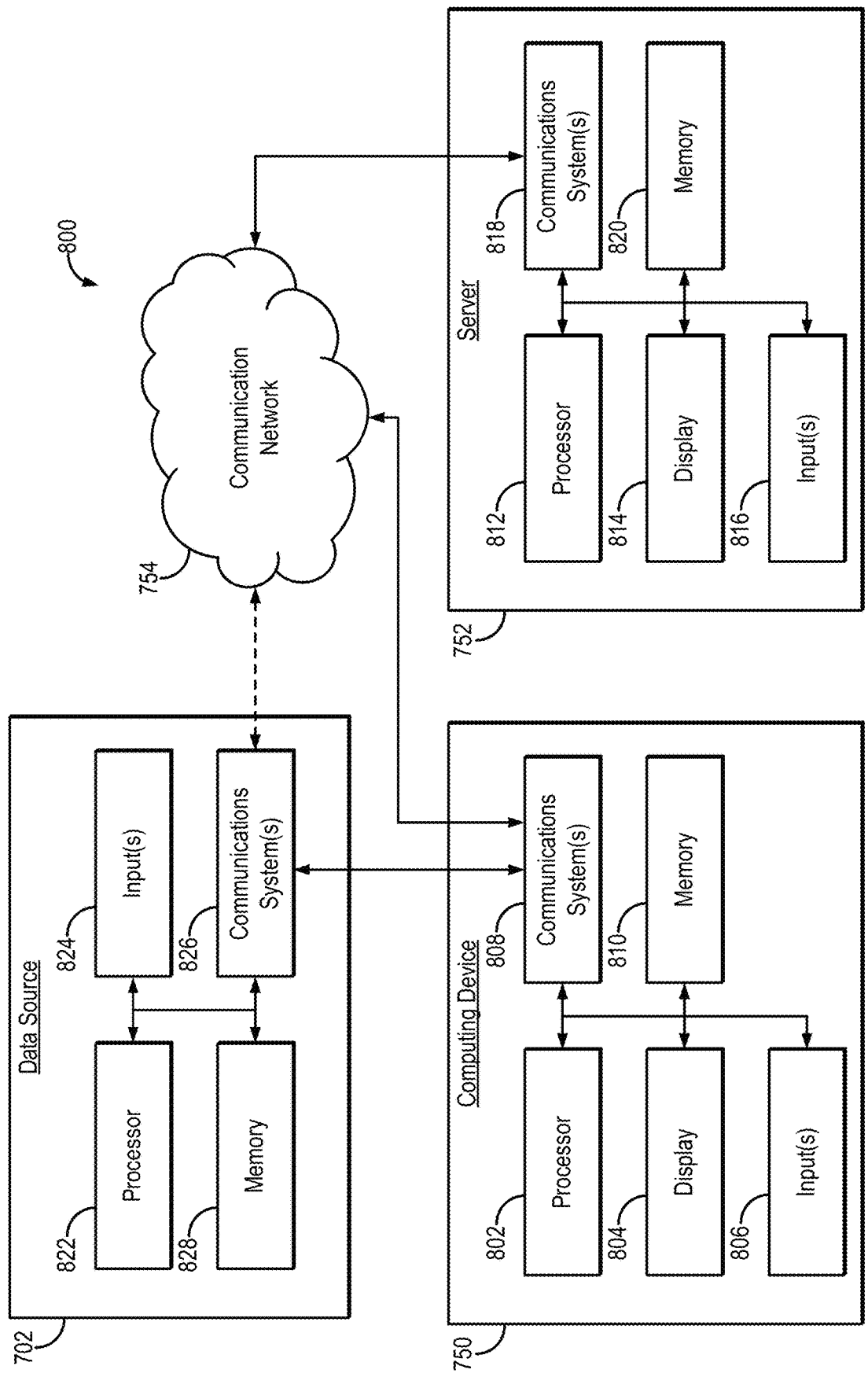
FIG. 8 is a block diagram illustrating example components that can implement the system shown in FIG. 7.

Referring now to FIG. 8, an example of hardware 800 that can be used to implement data source 702, computing device 750, and server 752 in accordance with some embodiments of the systems and methods described in the present disclosure is shown. As shown in FIG. 8, in some embodiments, computing device 750 can include a processor 802, a display 804, one or more inputs 806, one or more communication systems 808, and/or memory 810. In some embodiments, processor 802 can be any suitable hardware processor or combination of processors, such as a central processing unit ("CPU"), a graphics processing unit ("GPU"), and so on. In some embodiments, display 804 can include any suitable display devices, such as a computer monitor, a touchscreen, a television, and so on. In some embodiments, inputs 806 can include any suitable input devices and/or sensors that can be used to receive user input, such as a keyboard, a mouse, a touchscreen, a microphone, and so on.

In some embodiments, communications systems 808 can include any suitable hardware, firmware, and/or software for communicating information over communication network 754 and/or any other suitable communication networks. For example, communications systems 808 can include one or more transceivers, one or more communication chips and/or chip sets, and so on. In a more particular example, communications systems 808 can include hardware, firmware and/or software that can be used to establish a Wi-Fi connection, a Bluetooth connection, a cellular connection, an Ethernet connection, and so on.

In some embodiments, memory 810 can include any suitable storage device or devices that can be used to store instructions, values, data, or the like, that can be used, for example, by processor 802 to present content using display 804, to communicate with server 752 via communications system(s) 808, and so on. Memory 810 can include any suitable volatile memory, non-volatile memory, storage, or any suitable combination thereof. For example, memory 810 can include RAM, ROM, EEPROM, one or more flash drives, one or more hard disks, one or more solid state drives, one or more optical drives, and so on. In some embodiments, memory 810 can have encoded thereon, or otherwise stored therein, a computer program for controlling operation of computing device 750. In such embodiments, processor 802 can execute at least a portion of the computer program to present content (e.g., data plots, VIBES heat maps, images, user interfaces, graphics, tables), receive content from server 752, transmit information to server 752, and so on.

In some embodiments, server 752 can include a processor 812, a display 814, one or more inputs 816, one or more communications systems 818, and/or memory 820. In some embodiments, processor 812 can be any suitable hardware processor or combination of processors, such as a CPU, a GPU, and so on. In some embodiments, display 814 can include any suitable display devices, such as a computer monitor, a touchscreen, a television, and so on. In some embodiments, inputs 816 can include any suitable input devices and/or sensors that can be used to receive user input, such as a keyboard, a mouse, a touchscreen, a microphone, and so on.

In some embodiments, communications systems 818 can include any suitable hardware, firmware, and/or software for communicating information over communication network 754 and/or any other suitable communication networks. For example, communications systems 818 can include one or more transceivers, one or more communication chips and/or chip sets, and so on. In a more particular example, communications systems 818 can include hardware, firmware and/or software that can be used to establish a Wi-Fi connection, a Bluetooth connection, a cellular connection, an Ethernet connection, and so on.

In some embodiments, memory 820 can include any suitable storage device or devices that can be used to store instructions, values, data, or the like, that can be used, for example, by processor 812 to present content using display 814, to communicate with one or more computing devices 750, and so on. Memory 820 can include any suitable volatile memory, non-volatile memory, storage, or any suitable combination thereof. For example, memory 820 can include RAM, ROM, EEPROM, one or more flash drives, one or more hard disks, one or more solid state drives, one or more optical drives, and so on. In some embodiments, memory 820 can have encoded thereon a server program for controlling operation of server 752. In such embodiments, processor 812 can execute at least a portion of the server program to transmit information and/or content (e.g., data, images, a user interface) to one or more computing devices 750, receive information and/or content from one or more computing devices 750, receive instructions from one or more devices (e.g., a personal computer, a laptop computer, a tablet computer, a smartphone), and so on.

In some embodiments, data source 702 can include a processor 822, one or more inputs 824, one or more communications systems 826, and/or memory 828. In some embodiments, processor 822 can be any suitable hardware processor or combination of processors, such as a CPU, a GPU, and so on. In some embodiments, the one or more inputs 824 are generally configured to acquire data, images, or both, and can include a wearable or otherwise portable cardiac sensor that is capable of measuring both physical vibrations (e.g., via accelerometers, gyroscopes, and/or other inertial sensors) and electrocardiograms (e.g., via one or more electrodes or ECG-leads).

Additionally or alternatively, in some embodiments, the input(s) 824 can include any suitable hardware, firmware, and/or software for coupling to and/or controlling operations of a wearable or otherwise portable cardiac sensor. In some embodiments, one or more portions of the input(s) 824 can be removable and/or replaceable.

Note that, although not shown, data source 702 can include any suitable inputs and/or outputs. For example, data source 702 can include input devices and/or sensors that can be used to receive user input, such as a keyboard, a mouse, a touchscreen, a microphone, a trackpad, a trackball, and so on. As another example, data source 702 can include any suitable display devices, such as a computer monitor, a touchscreen, a television, etc., one or more speakers, and so on.

In some embodiments, communications systems 826 can include any suitable hardware, firmware, and/or software for communicating information to computing device 750 (and, in some embodiments, over communication network 754 and/or any other suitable communication networks). For example, communications systems 826 can include one or more transceivers, one or more communication chips and/or chip sets, and so on. In a more particular example, communications systems 826 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 828 can include any suitable storage device or devices that can be used to store instructions, values, data, or the like, that can be used, for example, by processor 822 to control the input(s) 824, and/or receive data from the input(s) 824; to generate images from data; present content (e.g., images, a user interface) using a display; communicate with one or more computing devices 750; and so on. Memory 828 can include any suitable volatile memory, non-volatile memory, storage, or any suitable combination thereof. For example, memory 828 can include RAM, ROM, EEPROM, one or more flash drives, one or more hard disks, one or more solid state drives, one or more optical drives, and so on. In some embodiments, memory 828 can have encoded thereon, or otherwise stored therein, a program for controlling operation of data source 702. In such embodiments, processor 822 can execute at least a portion of the program to generate images, transmit information and/or content (e.g., data, images) to one or more computing devices 750, receive information and/or content from one or more computing devices 750, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for generating a cardiac vibrational energy spectral heat map, the method comprising:
   (a) accessing physical vibration signal data with a computer system, the physical vibration signal data indicating physical vibrations measured from a subject and indicating cardiac motion of the subject;
   (b) accessing cardiac cycle timing data with the computer system, the cardiac cycle timing data indicating at least one of a timing or a duration of an event within a cardiac cycle of the subject;
   (c) computing a spectral energy map with the computer system, wherein the spectral energy map is computed from the physical vibration signal data acquired over a period of time determined from the cardiac cycle timing data; and
   (d) comparing the spectral energy map to normative data using the computer system, generating output as a cardiac vibrational energy spectral (VIBES) heat map that indicates deviations in vibration energy levels relative to the normative data.

2. The method as recited in claim 1, further comprising accessing with the computer system, electrocardiography (ECG) signal data acquired from the subject contemporaneously with the physical vibration signal data, and wherein accessing the cardiac cycle timing data includes computing the cardiac cycle timing data from the ECG signal data.

3. The method as recited in claim 1, wherein accessing the cardiac cycle timing data includes computing the cardiac cycle timing data from the physical vibration signal data.

4. The method as recited in claim 1, wherein accessing the cardiac cycle timing data includes accessing cardiac magnetic resonance imaging data and computing cardiac cycle timing data from the cardiac magnetic resonance imaging data.

5. The method as recited in claim 1, wherein accessing the cardiac cycle timing data includes accessing cardiac ultrasound data and computing cardiac cycle timing data from the cardiac ultrasound data.

6. The method as recited in claim 1, wherein the physical vibration signal data comprise seismocardiography (SCG) signal data.

7. The method as recited in claim 1, wherein computing the spectral energy map includes computing a short-time Fourier transform of the physical vibration signal data.

8. The method as recited in claim 1, wherein computing the spectral energy map includes computing a wavelet transform of the physical vibration signal data.

9. The method as recited in claim 1, wherein computing the spectral energy map with the computer system includes performing a spectral decomposition of the physical vibration signal data to analyze vibrational energy levels at different cardiac event times determined from the cardiac cycle timing data.

10. The method as recited in claim 1, wherein computing the spectral energy map with the computer system includes performing a spectral decomposition of the physical vibration signal data to analyze vibrational energy levels in one or more frequency ranges.

11. The method as recited in claim 10, wherein the one or more frequency ranges are selected from between 10 Hz and 240 Hz.

12. The method as recited in claim 11, wherein the one or more frequency ranges include a low-frequency range spanning 10 Hz to 60 Hz, a mid-frequency range spanning 60 Hz to 120 Hz, and a high-frequency range spanning 120 Hz to 240 Hz.

13. The method as recited in claim 11, wherein the one or more frequency ranges comprise a plurality of frequency ranges and at least two of the plurality of frequency ranges are at least partially overlapping.

14. The method as recited in claim 1, wherein the VIBES heat map indicates scores derived based on energy level percentiles determined based on comparing the spectral energy map to the normative data.

15. The method as recited in claim 1, wherein accessing the physical vibration signal data comprises acquiring the physical vibration signal data using a vibration sensor that is configured to be coupled adjacent the subject's heart.

16. The method as recited in claim 1, wherein the cardiac cycle timing data comprise at least one of a timing or a duration of a cardiac event selected from the group consisting essentially of systole, diastole, a cardiac valve opening, a cardiac valve closing, and an electrocardiography (ECG) complex.

17. The method as recited in claim 16, wherein the ECG complex includes at least one of a P-wave, a Q-wave, an R-wave, an S-wave, a T-wave, a QRS complex, a PR segment, an ST segment, a PR interval, or a QT interval.

* * * * *